United States Patent
Archer et al.

(10) Patent No.: US 10,655,103 B2
(45) Date of Patent: May 19, 2020

(54) EQUINE PROGENITOR CELLS

(75) Inventors: Charles William Archer, Aberdare (GB); Helen Elizabeth McCarthy, Cardiff (GB)

(73) Assignee: UNIVERSITY COLLEGE CARDIFF CONSULTANTS LIMITED, Cardiff (GB)

( * ) Notice: Subject to any disclaimer, the term of this patent is extended or adjusted under 35 U.S.C. 154(b) by 0 days.

(21) Appl. No.: 12/790,389

(22) Filed: May 28, 2010

(65) Prior Publication Data
US 2010/0291046 A1    Nov. 18, 2010

Related U.S. Application Data

(63) Continuation-in-part of application No. 12/526,194, filed as application No. PCT/GB2008/000393 on Feb. 6, 2008, now Pat. No. 8,357,534.

(30) Foreign Application Priority Data

Oct. 17, 2009 (GB) .................................. 0918234.6

(51) Int. Cl.
| | |
|---|---|
| *A61K 48/00* | (2006.01) |
| *C12N 5/077* | (2010.01) |
| *C12N 5/0775* | (2010.01) |
| *A61K 35/00* | (2006.01) |

(52) U.S. Cl.
CPC ......... *C12N 5/0655* (2013.01); *C12N 5/0668* (2013.01); *A61K 35/00* (2013.01); *C12N 2501/115* (2013.01)

(58) Field of Classification Search
CPC .............. C12N 5/0605; C12N 2506/02; C12N 5/0607; C12N 2506/03; C12N 2533/54; C12N 5/0678; C12N 2501/42; C12N 2502/025; C12N 2500/84; C12N 5/0662
USPC ....................................................... 435/325
See application file for complete search history.

(56) References Cited

U.S. PATENT DOCUMENTS

| | | | |
|---|---|---|---|
| 2004/0033212 A1* | 2/2004 | Thomson et al. | 424/93.7 |
| 2009/0093056 A1* | 4/2009 | Itskovitz-Eldor et al. | 435/372 |
| 2010/0291046 A1* | 11/2010 | Archer et al. | 424/93.7 |

OTHER PUBLICATIONS

Pacini et al. Suspension of Bone Marrow-Derived Undifferentiated Mesenchymal Stromal Cells for Repair of Superficial Digital Flexor Tendon in Race Horses. Tissue Engineering, 2007, vol. 13, pp. 2949-2956.*
Hendrickson et al. Chondrocyte-Fibrin Matrix Transplants for Resurfacing Extensive Articular Cartilage Defects. J. Orthopeadic Research, 1994, vol. 12, pp. 485-497.*
Hegewald et al. Hyaluronic acid and autologous synovial fluid induce chondrogenic differentiation of equine mesenchymal stem cells: a preliminary study.Tissue and Cell, 2004, vol. 36, pp. 431-438.*
Henson et al. Promotion of the intrinsic damageerepair response in articular cartilage by fibroblastic growth factor-2. OsteoArthritis and Cartilage, 2005, vol. 13, pp. 537-544.*
Stewart et al. Expression of p21CIP1/WAF1 in Chondrocytes. Calcified Tissue Int., 1997, vol. 61, pp. 199-204.*
Su, et al., "Cartilage-Derived Stromal Cells: Is It a Novel Cell Resource for Cell Therapy to Regenerate Infarcted Myocardium" Stem Cells, Feb. 2006, vol. 24, No. 2, pp. 349-356.
Alsalameh, et al., "Identification of Mesenchymal Progenitor Cells in Normal and Osteoarthritic Human Articular Cartilage" Arthritis & Rheumatism, vol. 50, No. 5, May 2004, pp. 1522-1532.
"Identification of subpopulations with characteristics of mesenchymal progenitor cells from human osteoarthritic cartilage using triple staining for cell surface markers" Fickert, et al., Arthritis Research & Therapy, 2004, vol. 6, No. 5, pp. R422-R432.
Heng, et al. "Directing Stem Cell Differentiation into the Chondrogenic Lineage in Vitro" Stem Cells; Alphamed Press, Dayton, Ohio, US; vol. 22, No. 7, Jan. 1, 2004, pp. 1152-1167.
Dowthwaite, et al. "The surface of articular cartilage contains a progenitor cell population" Journal of Cell Science, vol. 117, No. 6, Feb. 29, 2004, pp. 889-897.

* cited by examiner

Primary Examiner — Michael C Wilson
(74) Attorney, Agent, or Firm — King & Schickli, PLLC

(57) ABSTRACT

An isolated mammalian progenitor cell or its progeny, isolated from articular cartilage, is disclosed. Further is disclosed an equine progenitor cell isolated from the surface zone of equine articular cartilage tissue and uses thereof. Also disclosed are a method of tissue repair, a medicament, and a method of treating mammalian cartilage damage using such progenitor cells or progeny.

2 Claims, 6 Drawing Sheets
(4 of 6 Drawing Sheet(s) Filed in Color)

ual surface of joints (Archer and Francis-West, 2003). The principal role of the chondrocyte is in the maintenance of the intricate extracellular matrix of cartilage in particular the soluble, hydrophilic structures such as hyaluronan and aggrecan (Knudson, 2003). Intracellularly, the chondrocyte contains organelles that are typical of that of a metabolically active cell (Archer and Francis-West, 2003) that play a pivotal role in matrix synthesis, continually working to synthesise and turnover a large matrix to volume ratio, primarily composed of proteoglycans, glycosaminoglycans and collagens. Some chondrocytes also contain short processes or microvilli, which can detect mechanical alterations in the matrix. This is achieved as they extend from the cell directly into the matrix. Intracytoplastic filaments, lipid, glycogen and secretory vesicles enable chondrocytes to interact with the matrix. Mature chondrocytes are easily distinguished from other cells as they have a spheroidal morphology. They also have abundant amounts of type II collagen, large aggregating proteoglycans and specific non-collagenous proteins interwoven within a meshwork, which forms a cartilaginous matrix that covers and binds to their cell membranes.

Zones

Superficial Zone

EQUINE PROGENITOR CELLS

This application is a continuation-in-part of U.S. patent application Ser. No. 12/526,194, filed on Aug. 6, 2009, now U.S. Pat. No. 8,357,534 which in turn claims the benefit of priority in PCT Patent Application No. PCT/GB2008/000393 filed on Feb. 6, 2008, and further claims priority to British Provisional Patent Application No. GB0918234.6 filed on Oct. 17, 2009. The disclosures of each of the above-listed references are incorporated herein in their entirety by reference.

TECHNICAL FIELD

The invention relates to a novel equine progenitor cell or its progeny and in particular an articular cartilage equine progenitor cell or its progeny; a population of cells derived therefrom; a method for the production of said progenitor cell and said population of progenitor cells; the use of said progenitor cell and population of cells in tissue repair, and particularly connective tissue repair and more specifically joint repair; a medicament comprising said progenitor cell or said population of cells; and an implant comprising or including said progenitor cell or said population of cells.

BACKGROUND OF THE INVENTION

Articular cartilage is avascular, aneural and contains no lymphatic vessels. It has a low level of metabolic activity compared with that of other connective tissues such as muscle but can be considered active for a cell that relies largely on glycolosis for energy. It also has an extensive extracellular matrix, which it relies upon to provide cartilage with its characteristic properties of low friction, pain-free articulation. The two main constituents of articular cartilage are the highly specialised chondrocytes, which are unique to cartilage and the matrix, composed of a complex, interconnecting arrangement of proteoglycans, collagens and non-collagenous proteins.

Articular cartilage can be divided into four main zones through its depth. These are the superficial; transitional; upper and lower radial; and calcified cartilage zones running from the outer articular surface to the deep subchondral bone, respectively. Although named zones are present, there are no 'actual' boundaries, which can be visualised between the zones. In each zone there are biomechanical and morphological variations (Dowthwaite at al, 2004), which include differences in cell morphology (size and shape), cell packing, metabolic activity and the thickness of the layers. Differences in matrix composition also exist between zones, with variations in the types and quantities of various collagens, proteoglycans, and non-collagenous proteins.

In spite of articular cartilage being only a few millimetres thick, it still manages to provide resistance to compression and displays the ability to distribute loads, thus in turn, reducing high stresses placed upon subchondral bone.

Chondrocytes

Normal articular cartilage contains one cell type, the highly specialised chondrocyte surrounded by extracellular matrix. In the majority of cases, the chondrocyte is "cytoplasmically isolated" (Archer and Francis-West, 2003) from its adjacent cells, seldom forming cell-cell contacts except in the most superficial part of the tissue. Each chondrocyte, therefore, is completely surrounded by matrix with which it freely interacts. Chondrocytes differ in their morphology and metabolic activities between the zones of articular cartilage. Generally the chondrocyte has a rounded or polygonal morphology, except at tissue boundaries where it may appear flattened or discoid, i.e. at the artic The superficial zone (FIG. 6) is extremely thin and consists of two layers. The most superficial layer is acellular and consists of a thin, clear film of amorphous material known as the lamina splendens which overlies a sheet of fine, densely packed collagen type II microfibrils and comprises largely lubricin. The deeper cellular layer is composed of flattened, discoid chondrocytes enclosed within a collagen-rich matrix, which lie parallel to the articular surface (Dowthwaite et al, 2003). These cells synthesise matrix, which is abundant in collagen, fibronectin and water, and low in proteoglycans content compared to that of the deeper zones.

The dense layer of collagen fibrils have an orientation parallel to that of the surface and provide cartilage with its characteristic mechanical properties which include having high tensile strength and being able to resist shear force put upon it. The meshwork of collagen fibrils also permits the movement of molecules into and out of cartilage such as antibodies and large cartilage molecules, respectively.

Various studies have shown that the surface zone of articular cartilage is involved in the regulation of tissue development and growth. Developmental studies in our laboratory of *Monodelphis domestica* (South American opossum) have identified that articular cartilage grows by appositional growth from the articular surface (Hayes et al 2001) and that this method of growth allows for the distinct zonal architecture of this heterogeneous tissue to be established. These studies also showed that growth is driven by a slowly dividing population of chondrocytes in the surface zone of articular cartilage and a more rapidly dividing population of cells in the transitional zone (Hayes et al 2001). Not only do these observations account for the appositional nature of articular cartilage growth and zonal variation, they also suggest the presence of a specific articular chondrocyte progenitor cell population in the surface zone and a population of transit amplifying cells in the transitional zone.

Further, the surface zone has been found to be a signalling centre due to the expression of various growth factors and their receptors, which play a pivotal role in the morphogenesis of the diarthrodial joint via differential matrix synthesis (Dowthwaite et al, 2003). Recent in vitro studies have shown that the surface zone of bovine articular cartilage contains a progenitor cell population (Dowthwaite et al, 2004).

Acute articular cartilage injuries are a major concern for the athletic horse. They are a major cause of lameness and are associated with poor performance, early retirement and have a substantial negative economic impact. Chondral defects in the horse can occur through both disease and traumatic injury and if left untreated, leads to osteoarthritis characterised by progressive and permanent erosion of articular cartilage and associated bone and soft tissues of the joint.

Articular cartilage has a limited capacity for intrinsic repair. Partial thickness defects are non-healing and although full thickness defects may elicit an intrinsic healing response, the repair tissue formed is fibrocartilaginous and functionally inferior to the native tissue. Fibrocartilage is unsuitable as a replacement weight bearing surface and has been shown to undergo mechanical failure with use. Depending on the location and extent of the initial lesion, arthroscopic surgical debridement may be an effective treatment for returning a horse to athletic soundness. In many cases, however, additional techniques are needed to improve the healing response in the cartilage so as to preserve articular cartilage function.

A number of surgical treatments in the horse have been attempted both clinically and in experimental situations. Microfracture is a surgical procedure whereby the subchondral bone is perforated allowing mesenchymal stromal cells, blood cells and growth factors access to the chondral lesion. However, there is often poor integration, fibrocartilage formation and an aggrecan content that is not comparable to normal cartilage.

Cell based therapies are currently the treatment of choice for human articular cartilage repair but so far has limited use in the horse. Arguably, the current 'gold standard' for the biological repair of human chondral defects is autologous chondrocyte implantation (ACI). After monolayer expansion, the chondrocytes are placed within the chondral defect either by being injected through a periosteal flap that has been sutured over the lesion or by placing the cells on a collagenous membrane, which is secured within the lesion (matrix assisted chondrocyte implantation MACI). In either case, a limitation of the technique is that only relatively small lesions can be treated. When human chondrocytes undergo approximately 7 population doublings, they lose the ability to re-express the chondrogenic phenotype (in culture), thus limiting cell availability and this in turn is dependant on the amount of cartilage that can be harvested from the joint periphery which again is limited. However, the number of population doublings required for equine chondrocytes to lose chondrogenic potency has yet to be established. Successful repair of full thickness equine cartilage defects have been reported 12 and 18 months post-operatively using chondrocyte seeded scaffolds (Barnewitz et al., 2006, Frisbie et al., 2007). Articular chondrocytes and mesenchymal stromal cells (stem cells) are the two main cell sources used in cell-based cartilage repair therapies. It is unclear at this time however, if one cell type is more suitable than the other.

As mentioned above, others have previously isolated a population of progenitor cells from the surface zone of bovine articular cartilage (Dowthwaite et al., 2004). These cells were isolated using differential adhesion to fibronectin. They were able to form colonies from an initially low seeding density and were able to expand in culture without losing their chondrogenic phenotype. These cells were also engrafted into other connective tissue lineages and maintained the ability to form cartilage when transferred in to a 3D pellet culture system. Additionally, US patent 2006/0239980 teaches that articular cartilage obtained from the surface zone of human cartilage tissue can be enzymatically digested to produce a population of chondrocytes which, through culturing, can be dedifferentiated into chondroprogenitor tissue. However, there is no data in either of these documents concerning the phenotypic stability of this tissue and therefore the use of this bovine or human tissue as a reliable source of material for tissue repair is questionable.

Recently, we have extended the aforementioned studies and discovered, to our surprise, that it is possible to isolate a population of equine articular cartilage progenitor cells from the surface zone that have surprising and advantageous characteristics.

Here, equine articular cartilage progenitor cells (ACPC) and equine bone marrow-derived stromal cells (BMSC) are compared as potential cell sources for mammalian cartilage repair and, in particular equine cartilage repair. The study reports the isolation and partial characterisation of ACPC and compares their differentiation capacity to BMSC in vitro. We discovered that whilst ACPC and BMSC have functional equivalence in their multipotent differentiation capacity, to our surprise, chondrogenic induction of ACPC did not result in a hypertrophic cartilage phenotype, unlike BMSC. This means the ACPC retained the highly desirable hyaline cartilage phenotype. In contrast, after chonodrogenic induction BMSC exhibited a hypertrophic cartilage phentotype which is disadvantageous to any cartilage repair procedure as the cells can undergo terminal differentiation ultimately resulting in mineralisation of the matrix tissue, so producing stiffened joints. Therefore, equine ACPC have the highly desirable and, as yet, undemonstrated (in other cartilage stem/progenitor cells) phenotypic stability that makes them a reliable source of material for tissue repair.

Additionally, our novel equine progenitor cells exhibit phenotypic plasticity in that these cells can be functionally induced into various connective tissue types in order to produce different sorts of connective tissue.

It follows that our equine progenitor cells have significant use in cartilage repair. However, our progenitor cells could be used for the repair of other forms of connective tissue such as ligament, skin or bone.

Further, although our progenitor cells are suited to autologous repair, particularly cartilage repair, these cells also could be used allogeneically since many other stem cells have been shown to be immunosuppressive.

SUMMARY OF THE INVENTION

According to a first aspect of the invention there is provided an isolated articular cartilage equine progenitor cell or its progeny.

Reference herein to a progenitor cell includes reference to a dividing cell with the capacity to differentiate, it includes putative stem cells in which self-renewal has not yet been demonstrated.

In a preferred embodiment of the invention said progenitor cell is isolated from the surface zone of equine cartilage tissue.

According to a yet further aspect of the invention there is provided an equine progenitor cell or its progeny which is characterised by any one or more, including any combination, of the following traits:
1. its isolation from the surface zone of equine articular cartilage;

2. its isolation by high affinity adhesion to fibronectin or a fragment thereof containing the RGD sequence;
3. a population doubling at a rate of approximately one per day;
4. the ability to differentiate into any connective tissue type;
5. the expression of any one or more of the following putative stem cell markers: Notch-1, CD90 or CD166;
6. the expression of Type I and Type II collagen but not Type X collagen following chondrogenic induction.

According to a further aspect of the invention there is provided an equine progenitor population as deposited at the European Collection of Cell Cultures (ECACC), Centre for Emergency Preparedness and Response, The Health Protection Agency, Porton Down, Salisbury SP4 0JG under Accession No. 09101301 13 Oct. 2009.

According to a yet further aspect of the invention there is provided a population of equine connective tissue cells derived from the aforementioned progenitor cell.

According to a further aspect of the invention there is provided the use of the aforementioned described progenitor cell or its progeny in tissue repair.

According to a further aspect of the invention there is provided the use of a population of equine connective tissue cells, derived from the progenitor cell described herein, in tissue repair.

According to a further aspect of the invention there is provided an implant for use in tissue repair comprising a progenitor cell as described herein, or its progeny, or a population of cells derived from said cell or its progeny.

According to a further aspect of the invention there is provided a medicament comprising the afore progenitor cell or its progeny, or a population of cells derived therefrom.

According to a further aspect of the invention there is provided a method of treating mammalian cartilage damage comprising: administering or implanting the progenitor cell of the invention, or its progeny, or a population of cells derived therefrom, into a site of a mammal to be treated.

Ideally said mammal is equine, canine, feline or human.

According to a further aspect of the invention there is provided a method for isolating an equine progenitor cell or its progeny comprising:
a) obtaining equine articular cartilage tissue from the surface zone of equine articular cartilage;
b) digesting the tissue to release chondrocytes, by using enzymes;
c) exposing the isolated chondrocytes to fibronectin and/or a fragment thereof containing RGD sequence; and
d) isolating those cells that bind fibronectin or said fragment;
e) optionally, culturing the isolated cells to obtain said progeny.

In a preferred method of the invention said released chondrocytes are cultured on fibronectin or a RGD sequence, such as a fragment of fibronectin containing said sequence.

In a further preferred method of the invention said articular cartilage is digested with a combination of pronase and collagenase and more preferably the articular cartilage is exposed to 1% pronase or 700 international units/ml, for ideally 12-17 minutes and most ideally 15 minutes at 37° C. followed by exposure to 300 international units/ml of collagenase, for ideally 2-5 hours and most ideally 3 hours at 37° C.

In yet a further aspect of the invention the digested chondrocytes are either filtered and/or centrifuged in order to isolate the chondrocytic tissue.

Where centrifugation takes place it is undertaken at 500×g for 5 minutes.

Isolated chondrocytes, preferably, are then seeded into wells coated with fibronectin. After a short period, approximately 20 minutes, the media plus any non-adherent cells are removed and replaced with growth medium. Then colonies are selected for cloning.

In a preferred method of the invention step e) involves culturing said cells under selected conditions to provide for differentiation thereof into at least one selected phenotype. Those skilled in the art will appreciate that the nature of the culture conditions can be specifically selected for this purpose as shown in the Examples described herein.

These and other embodiments, aspects, advantages, and features will be set forth in the description which follows, and in part will become apparent to those of ordinary skill in the art by reference to the following description of the invention and referenced drawings or by practice of the invention. The aspects, advantages, and features of the invention are realized and attained by means of the instrumentalities, procedures, and combinations particularly pointed out in the appended claims. Unless otherwise indicated, any patent and non-patent references discussed herein are incorporated in their entirety into the present disclosure specifically by reference.

BRIEF DESCRIPTION OF THE DRAWINGS

The accompanying drawings, incorporated herein and forming a part of the specification, illustrate several aspects of the present invention and together with the description serve to explain certain principles of the invention. The patent or application file contains at least one color photograph. Copies of this patent or patent application publication with color photograph(s) will be provided by the Office upon request and payment of the necessary fee. In the drawings.

DETAILED DESCRIPTION OF THE INVENTION

Figure 1:
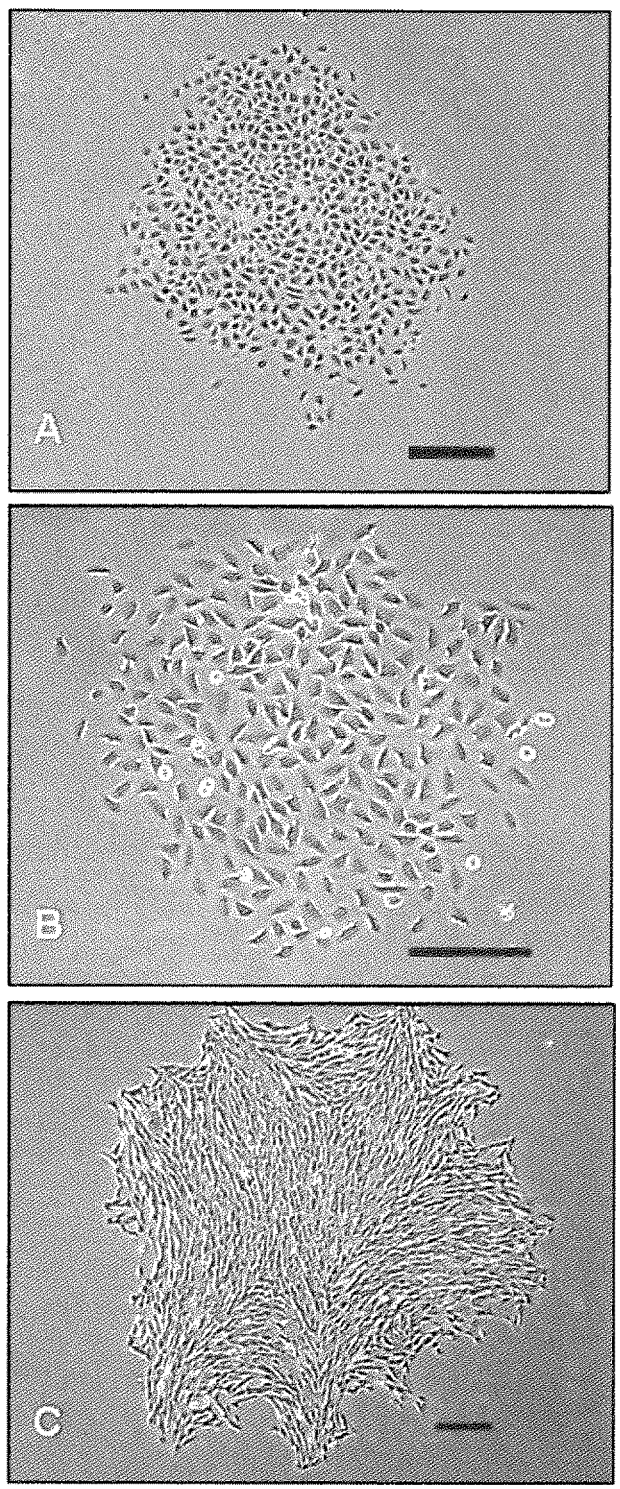
FIG. 1 shows ACPC colonies 6 days after single cell isolation×10 (A), ×20 (B). BMSC colony (C) observed 8 days after single cell isolation (×10). Scale bars: 50 µm.

In the following detailed description of the illustrated embodiments, reference is made to the accompanying drawings that form a part hereof, and in which is shown by way of illustration, specific embodiments in which the invention may be practiced. These embodiments are described in sufficient detail to enable those skilled in the art to practice the invention. Also, it is to be understood that other embodiments may be utilized and that process, materials, reagent, and/or other changes may be made without departing from the scope of the present invention.

Materials And Methods Equine Bone Marrow Stromal Cells Equine BMSC were isolated from bone marrow stroma aspirates from the metacarpal bone (MC III) using the classical plastic adhesion method. Briefly, bone marrow was extracted under sterile conditions and blasted with serum free medium (DMEM with 4500 mg/l glucose and GlutaMAX-1™ [DMEM-HG/GM] plus 100 μg ml$^{-1}$ Gentamicin and 10 mM HEPES buffer) to liberate the cellular constituents. The cell solution was allowed to separate into a lipid and aqueous layer after which the aqueous layer (containing the BMSC) was filtered through a 40 μm nylon cell strainer. After centrifugation at 500×g for 5 minutes, the supernatant was discarded and the cell pellet resuspended in serum free medium. Cells and medium were transferred into culture flasks and incubated at 37° C. at 5% $CO_2$. Cells were allowed to settle for 4 days to allow for attachment. After 4 days flasks were washed thoroughly to ensure removal of all non-adherent cell types. Cells were incubated at 37° C. at 5% $CO_2$ and received growth media changes every 48 hours. Growth media consisted of serum free medium plus 10% foetal bovine serum (FBS) and 10 ng ml$^{-1}$ fibroblastic growth factor-2 (FGF-2. Peprotech, USA).

Equine Articular Cartilage Progenitor Cells

Equine surface zone cartilage was harvested from the medial and lateral condyles of the distal end of MC III. Small, isolated cartilage defects typically seen in working horses were present in a minority of joints and avoided during tissue harvesting.

Chondrocytes were isolated by a sequential 700 i.u·ml$^{-1}$ pronase and 300 i.u·ml$^{-1}$ collagenase digestion as previously described (Archer et al., 1990). Following enzymatic digestion the cell suspension was filtered through a 40 μl cell strainer and centrifuged at 500×g for 5 minutes. Chondrocytes were re-suspended in 1 ml serum free medium (DMEM/F12 with GlutaMAX-1υ plus 100 μg ml$^{-1}$ Gentamicin, 0.1 mM ascorbate-2-phosphate and 10 mM HEPES buffer) and counted using a haemocytometer.

With the aim of isolating a progenitor population, a differential adhesion onto fibronectin was performed (Jones and Watt, 1993; Dowthwaite et al., 2004). Six-well culture plates were pre-treated with 1% bovine fibronectin (FN) solution diluted in sterile PBS/ACE (1 mM $CaCl_2$ and 1 mM $MgCl_2$ distilled water+PBS, sterile filtered) and incubated overnight at 4° C.

Chondrocytes were seeded at 4000 cells per ml$^{-1}$ with 1 ml added per well and incubated at 37° C. at 5% $CO_2$ for 20 minutes in serum free medium. After 20 minutes, the media plus non-adherent cells were carefully removed and replaced with growth medium (serum free medium plus 10% FBS). On day 6, colonies that consisted of greater than 32 cells were marked for cloning. A population of more than 32 cells was chosen as this number indicates that the colony derived from more than 5 population doublings of a single cell. The original cell can therefore be discounted as a transit amplifying cell and assumed to be a progenitor (Jones and Watt, 1993). Colonies were isolated using polystyrene cloning cylinders (Sigma-Aldrich, UK), trypsinised and transferred into 12-well plates containing growth medium with the addition of 10 ng ml$^{-1}$FGF-2. Clones were cultured until confluent then passaged accordingly.

Immunocytochemical Analysis of Monolayer Cultures

In order to characterise the BMSC and ACPC, cells were fixed and labelled with antibodies for CD90 (BD Biosciences, UK) and CD166 (Serotec, UK). Additionally, Notch-1 expression of BMSC and ACPC was determined using the Notch-1 C-20 antibody (Santa Cruz Biotechnology Inc. UK). Monolayer cultures of ACPC and BMSC were washed with PBS, fixed in 4% paraformaldehyde for 5 minutes and air dried. Following a 30-minute incubation with 0.2% Triton-X (Sigma-Aldrich) diluted in PBS, cells were rehydrated in PBS/T (PBS+1% Tween 20; polyethylenesorbitan monolaurate; Sigma-Aldrich) for 5 minutes then blocked for one hour with (a) 5% normal goat serum for CD90 and CD166 (b) 5% normal rabbit serum for Notch-1 at room temperature.

Primary antibodies diluted in PBS/T (CD90 5 μg ml$^{-1}$, CD166 and Notch-1 C20 10 μg ml$^{-1}$) were incubated with the cells at 4° C. overnight. Appropriate species specific IgG immunoglubulins diluted in PBS/T (5 μg ml$^{-1}$) and PBS served as negative controls. After washing in PBS/T, relevant FITC conjugated secondary antibodies diluted in PBS/T (10 μg ml$^{-1}$) were incubated for 1 hour at room temperature. Goat anti-mouse FITC conjugated secondary antibody was applied to CD90 and CD166 treated cells (including controls). Rabbit anti-goat FITC conjugated secondary antibody was applied to Notch-1 treated cells (including controls). Dishes were washed thoroughly with PBS and mounted onto slides with Vectorshield® mounting media containing 4',6-diamidino-2-phenylindole (DAPI) (Vector laboratories, UK). Fluorescent labelling was observed and photographed using an Olympus BX61 microscope.

Chondrogenic Differentiation

To compare the chondrogenic ability of BMSC and ACPC, cells were cultured in chondrogenic medium in pellet mass culture. Briefly, cells were harvested and resuspended in chondrogenic medium consisting of DMEM-HG/GM, plus 2% FBS, 100 μg ml$^{-1}$ Gentamicin, 10 mM HEPES buffer, 10 μg ml$^{-1}$ ITS, 0.1 mM ascorbate-2-phosphate, 10 nM dexamethasone and 10 ng ml$^{-1}$ transforming growth factor beta-1 (TGF-β1, Peprotech). Cells were placed in 1.5 ml tubes and centrifuged at 500×g for 5 minutes to form a pellet consisting of 0.5×10$^6$ cells. Pellets were incubated at 37° C. and 5% $CO_2$ and media changed every three days.

After 21 days, chondrogenic pellets were fixed in neutral buffered formalin solution, photographed and embedded into paraffin wax, immunohistochemistry on the chondrogenic pellets was performed for aggrecan and collagen types I, II and X. Briefly, pellet sections were blocked with the appropriate serum for 30 minutes at room temperature. Excess serum was removed and the sections were incubated with the primary antibodies, aggrecan-IGD; 6B4 (kind gift from Professor Bruce Cater son, Cardiff University), collagen type I (10 μg ml$^{-1}$; Abcam, UK), collagen type II (10 μg ml$^{-1}$; DSHB, USA) and collagen type X (10 μg ml$^{-1}$; Abcam) in PBS/T overnight at 4° C., Sections were then washed in PBS/T and incubated with appropriate FITC-conjugated secondary antibodies (10 μg ml$^{-1}$) for 1 hour at room temperature. After 3 washes in PBS, sections were mounted under a coverslip using either Vectorshield® mounting medium containing propidium iodide (PI) or DAPI. Images were viewed and recorded using either the SPE1000 Confocal microscope system (Leica Microsystems, UK) or an inverted fluorescence microscope (Olympus BX61). At each experimental run, the appropriate immunoglobulin (10 μg ml$^{-1}$) replaced the primary antibody, as a negative control. For 6B4+, collagen type II and collagen type X, sections were subjected to a chondroitinase (0.25 U ml$^{-1}$; Sigma-Aldrich) and hyaluronidase (2 U ml$^{-1}$; Sigma-Aldrich) pre-treatment for 1 hour at 37° C. For collagen type I, cells were subjected to Proteinase K (2.0 μg ml$^{-1}$; Sigma-Aldrich) digest for 15 minutes.

Osteogenic Differentiation

Pellet cultures were established as described above. Osteogenic differentiation medium comprised of DMEM-HG/GM, 10% FBS, 10 mM β-glycerophosphate, 10 nM dexamethasone and 0.1 mM L-ascorbic-acid-2-phosphate. Pellets were incubated at 37° C. and 5% $CO_2$ and media changed every three days.

After 21 days, osteogenic pellets were fixed in neutral buffered formalin solution, photographed and processed into Technovit 9100 New® (TAAB Laboratories, UK) using the chemical catalytic method fully described by Yang et al., (2003) with fully destabilised resin at all steps as recommended by Singhrao et al., (2009). Pellets were sectioned using glass knives to a thickness of 1 μm as previously described (Singhrao et al., 2009). Sections were de-acrylated in 2-methoxyethyl acetate (Sigma-Aldrich) for 3-4 h followed by rehydration through xylene, a series of graded ethanol to distilled water. Resin autofluorescence was quenched by immersing tissue sections in 1% sodium borohydride and equilibrated in PBS as previously described (Singhrao et al., 2009).

Rehydrated, de-acrylated pellet sections were stained to assess the mineral content using the von Kossa silver impregnation technique (5% aqueous silver nitrate for 30 minutes under bright light, 5% sodium carbonate in 25% formalin for 5 minutes and 5% sodium thiosulphate for 2 minutes with water washes in between). Examination and images were recorded using the Leitz DMRB light microscope (Leica Microsystems, UK).

For immunolabelling with osteocalcin, the rehydrated pellet sections were digested with 5 mg/ml bovine testes hyaluronidase (Sigma-Aldrich)/PBS for 1 h at 37° C. Sections were treated to blocking reagent for 1 hr in PBS/T+ 0.5% normal rabbit serum (X0902, DakoCytomation). The tissue sections were incubated with goat anti-osteocalcin (Santa Cruz Biotechnology Inc) diluted 20 μg ml$^{-1}$ in the blocking reagent and incubated at 4° C. overnight. The appropriate immunoglobulin (10 μg ml$^{-1}$) replaced the primary antibody, as a negative control. Following overnight incubation, the sections were incubated for 1 h at room temperature in secondary detection antibody conjugated to rabbit anti-goat-FITC (F02016, Sigma-Aldrich) at 5 mg/ml diluted in blocking buffer. Sections were mounted under a coverslip using Vectorshield® containing PI. Examination and images were recorded using the SPE1000 confocal microscope system (Leica Microsystems)

Adipogenic Differentiation

Adipogenic differentiation was induced in 2-D monolayer cultures using a modified protocol described by Koch et al. (2007). Briefly, cells were seeded in 6 well plates at 5×10$^4$ cells per well and cultured in growth medium until subconfluent. Cells were then treated with DMEM-HG/GM plus 10 μg ml$^{-1}$ insulin, 1 μM dexamethasone, 100 μM indomethacin, 500 μM 3-isobutyl-1-methyl xanthine (IBMX) and 15% normal rabbit serum with medium changes taking place every 2 days. Wells treated with growth medium were also set up as negative controls. After 6 days exposure to adipogenic induction medium, the cells were fixed with neutral buffered formalin solution and stained with Oil red O for the presence of lipid droplets (Barbero et al., 2003). Cells were counterstained with haematoxylin for 1 minute.

Results

ACPC were isolated by differential adhesion onto fibronectin. Adherent cells formed a large number of colonies from a low seeding density. Colonies were observed 6 days after initial seeding and were subsequently expanded in monolayer culture (FIGS. 1a & 1b). BMSC formed colonies on adherence to plastic-bound serum proteins (FIG. 1c). BMSC exhibited a higher rate of proliferation indicated by an average of 21 population doublings in 14 days, whilst ACPC undertook on average 22 population doublings in 21 days. There was no indication of senescence in either cell type at this stage.

Immunohistochemistry of Clonally Derived BMSC and ACPC

Figure 2:
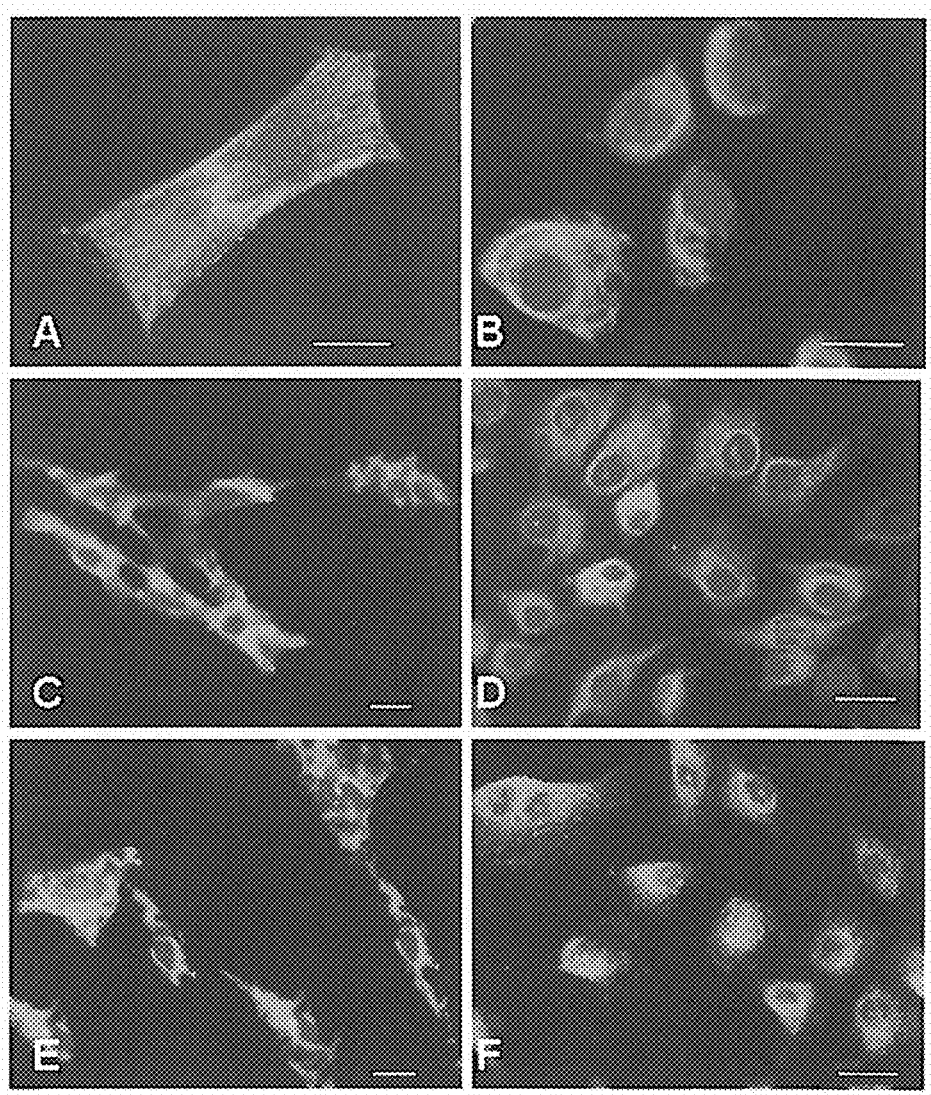
FIG. 2 shows immunohistochemical labelling of monolayer cultures of BMSC (A, C, E) and ACPC (B, D, F). CD90 (A,B), CD166 (C,D) and Notch1 (E,F). Scale bars: 25 µm.

Immunolabelling of monolayer cultures demonstrated that both ACPC and BMSC expressed the putative stem cell markers CD90 (FIGS. 2a & 2b) and CD166 (FIGS. 2c & 2d) in addition to the cell fate selector gene, Notch-1 (FIGS. 2e & 2f). The majority of cells positively labeled in all ACPC colonies in addition to expanded BMSC. Differences in labelling intensity between cells were observed.

Chondrogenic Differentiation

Chondrogenic induction of both cell types produced pellets that were smooth and iridescent in appearance (FIGS. 3a & 3b) and stained positively for toluidine blue and safranin O (images not shown). BMSC pellets were spherical and generally larger than ACPC pellets which were also more varied in size and shape. There was some evidence of zonal organisation in pellets from both cell types indicated by flattened cells at the surface and rounder cells towards the centre (images not shown).

Figure 3:
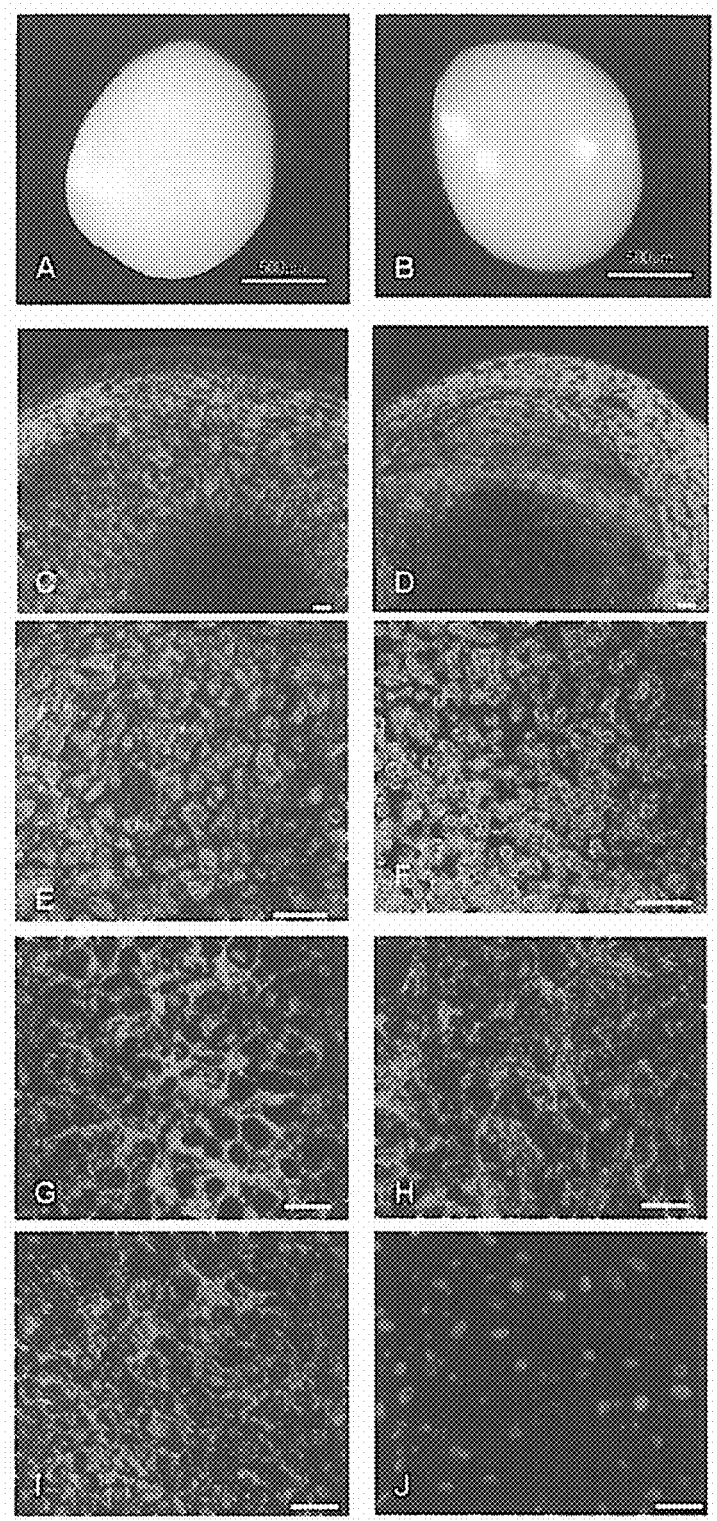
FIG. 3 shows chondrogenic induction of BMSC (A, C, E, G, I) and ACPC (B, D, F, H, J). Gross morphology of 3D pellet cultures (A,B), type II collagen labelling (C,D), Aggrecan labelling (E,F), ), type I collagen labelling (G,H) and type X collagen labelling (I,J). Scale bars: 50 µm unless otherwise stated.

Immunohistochemistry revealed positive labelling for type II collagen (FIGS. 3c & 3d), aggrecan (FIGS. 3e & 3f) and type I collagen (FIGS. 3g & 3h), Type X collagen was not detected in ACPC pellets but was detected in all BMSC pellets representing a terminal cartilage phenotype (FIGS. 3i & 3j).

Osteogenic Differentiation

Figure 4:
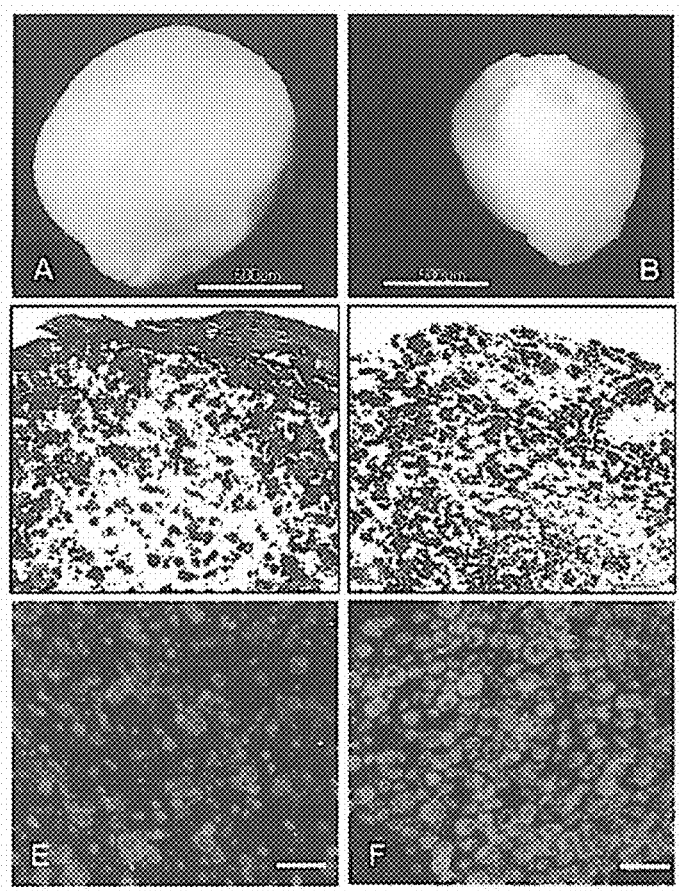
FIG. 4 shows osteogenic induction of BMSC (A, C, E) and ACPC (B, D, F). Gross morphology of 3D pellet cultures (A,B), positive von Kossa staining (C,D) and positive osteocalcin labelling (E,F). Scale bars: 50 µm unless otherwise stated.

Osteogenic induction of ACPC and BMSC produced pellets that were irregular and matt in appearance (FIGS. 4a & 4b) and were positive upon von Kossa staining (FIGS. 4c & 4d). Immunohistochemistry revealed positive labelling for osteocalcin suggesting bone formation (FIGS. 4e & 4f).

Adipogenic Differentiation

Figure 5:
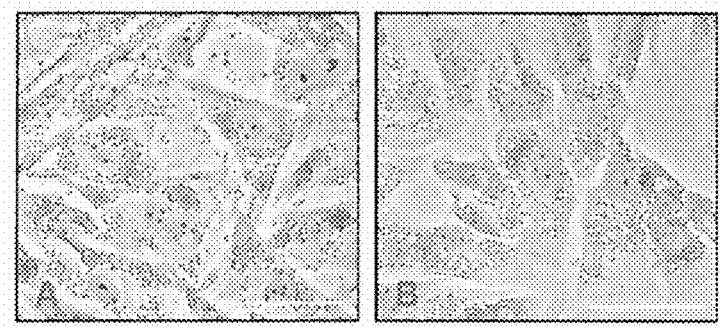
FIG. 5 shows adipogenic induction of BMSC (A) and ACPC (B). Lipid droplet deposition stained with Oil Red O. Scale bars: 50 µm.
Figure 6:
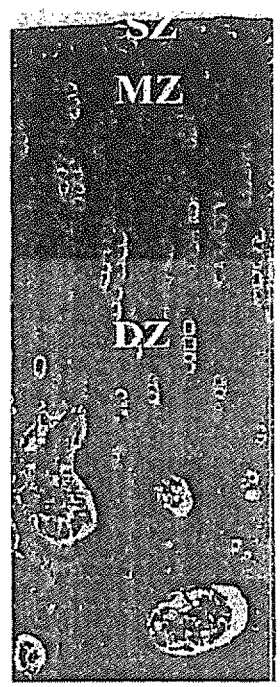
FIG. 6 shows a section through cartilage tissue.

Adipogenic induction in both cell types revealed a positive result via oil red O staining (FIG. 5). In the negative controls kept in growth medium, no lipid staining was detectable in either cell type.

Discussion

Articular chondrocytes and mesenchymal stromal cells are the two main cell sources used in cell-based cartilage repair therapies; however, it is unclear if one is more suitable than the other. Here, equine ACPC and BMSC were isolated, partially characterised and their differentiation potential compared and contrasted.

As yet, there is no unique equine mesenchymal stem cell marker. Here, BMSC expressed CD90, a putatative mesenchymal stem cell marker associated with bone marrow-derived, adipose-derived and umbilical cord-derived equine stem cells (Stephan et al., 2007; Pascucci at al., 2007; Hoynowski et al., 2007). Additionally, BMSC were further characterised by the expression of CD166, a putatative human stem cell marker, thus demonstrating cross-reactivity between the two species. In comparison to BMSC, ACPC demonstrated similar expression of the chosen cell membrane markers. They expressed both CD90 and CD166, thus providing further evidence for their progenitor/stem cell status.

The cell-fate signalling receptor, Notch-1 was also found to be expressed by both BMSC and ACPC. Although not a unique marker of ACPC, Notch-1 signalling has been previously implicated in the maintenance of clonality and proliferation of bovine ACPC (Dowthwaite et al., 2004). In situ, it has been suggested that Notch 1 signalling may play one of two roles in the surface zone of articular cartilage; it may function to maintain cells in a proliferative state, or it may promote chondrocyte differentiation and cartilage growth (Dowthwaite at al., 2004). Notch 1 has also been implicated in tissue boundary specification and its expression at the articular surface is consistent with this role (Williams et al., 2009). Furthermore, Notch 1 has also been implicated during the initial stages of chondrogenesis in human bone marrow stromal cells (Oldershaw at al., 2007). It is, therefore, suggested that Notch 1 is a possible candidate marker for cell selection in cartilage repair procedures.

ACPC were found to have the capacity to proliferate extensively in vitro in the presence of FGF-2 and, like BMSC, maintain their morphological and growth characteristics over the study period. Previous reports have demonstrated a population doubling time of 6 days for normal equine chondrocytes (Nixon et al., 1992). Here, we show that ACPC have a population time more akin to BMSC with the former having a population doubling time of 1 day as, on average, they undertook 22 population doublings in 21 days. BMSC exhibited a slightly higher rate of proliferation indicated by an average of 21 population doublings in 14 days, and hence a population doubling time of less than 1 day.

Both ACPC and BMSC have demonstrated pluripotency via differentiation into chondrogenic, osteogenic and adipogenic lineages. Under chondrogenic differentiation, ACPC pellets demonstrated a proteoglycan rich matrix, type II collagen expression and a lack of type X collagen, confirming a hyaline cartilage phenotype. BMSC also demonstrated a proteoglycan rich matrix, with type II collagen but type X collagen was also detected which suggested differentiation into terminally differentiated chondrocytes and thus the formation of a hypertrophic cartilage. Hypertrophic cartilage is formed during the late stages of endochondral ossification, whereby mesenchymal cells differentiate through a series of cellular phenotypes into type X collagen synthesising hypertrophic chondrocytes before undergoing cell death. Subsequent vascular in-growth from the perichondrium allows the infiltration of osteoblasts which replace the tissue with a mineralised bone matrix. (Lefebvre and Smits, 2005). Hypertrophic cartilage not only lacks the specialised functional properties of hyaline cartilage but could also lead to the formation of mineralised bone and would, therefore, be detrimental to any cartilage repair procedure.

Under chondrogenic differentiation, both cell types expressed type I collagen. Given the occurrence of significant amounts of type II collagen in pellets from both cell types, it has been suggested that the matrix remodels from a fibrocartilage to a hyaline type cartilage with time in culture which is also seen in normal cartilage differentiation in the embryo (Craig et al., 1987). It has also been questioned whether the presence of type II collagen alone is a valid marker of cartilage repair quality (Roberts et al., 2001). A more recent cartilage repair study revealed 78% of cartilage biopsies had a fibrocartilaginous repair tissue (Roberts et al., 2003). Notably, the average time interval between graft and biopsy was greatest for biopsies of hyaline compared to fibrocartilage tissue which suggests that the initial repair tissue may be fibrocartilaginous, but may remodel over time to become more 'hyaline-like.' All the same, in this study, both BMSC and ACPC expressed type I and type II collagen in this study with no apparent differences observed between the two cell types.

Under osteogenic differentiation both cell types demonstrated evidence of mineralisation via von Kossa staining and positive osteocalcin immunolabelling. Osteogenic differentiation has previously been reported in equine bone marrow-derived, adipose-derived umbilical cord-derived stem cells and equine peripheral blood derived progenitors (Stephan et al., 2007; Pascucci et al., 2007; Hoynowski et al., 2007, Koerner et al., 2006). We are, however, the first to report osteogenic differentiation of equine cells in 3D culture. Marrow stromal cells have been previously described to enhance bone repair in human studies (Quarto et al., 2001; Marcacci et al., 2007; Morishita et al., 2006) and although further molecular characterisation is required, ACPC have clinical implications to augment equine bone repair and regeneration.

Our findings for adipogenic differentiation are comparable to other recently published studies. We found that the addition of 15% rabbit serum significantly enhanced adipogenic differentiation in both cell types. Our work confirmed that of Janderova et al. (2003), who also demonstrated that by using 15% rabbit serum instead of foetal calf serum, over 90% of all human marrow stromal cells were oil red O positive within 6 days of adipogenic induction. We can conclude that there were no apparent differences observed between the two cell types for adipogenic differentiation.

In addition to presenting a novel cell source for equine cartilage repair, ACPC may be of great use in research targeting cartilage repair in humans. The horse represents a superior animal model for human cartilage repair for many reasons including similarity of joint anatomy and size and articular cartilage thickness. An ability to create multiple defects, as demonstrated in the trochlear ridge model, allows the comparison of different cell-based repair therapies and enhanced experimental throughput (Frisbie et al., 2007). Unlike smaller animal models, horses are athletic and, therefore, demonstrate comparable functional needs to humans. In addition, the ability to control exercise and monitor clinical recovery post-operatively improves the long term assessment of cartilage repair techniques (Frisbie at al., 2007).

CONCLUSIONS

We have demonstrated the first isolation of equine chondroprogenitors. Equine ACPC and BMSC demonstrated functional equivalence in their multipotent differentiation capacity. However, chondrogenic induction of equine ACPC did not result in a hypertrophic cartilage phenotype, therefore, equine ACPC are considered desirable in producing cartilage capable of functional repair. Additionally, ACPC hold an advantage over normal chondrocytes as they can divide to produce more cells at a faster rate and maintain their phenotype when cultured extensively.

The foregoing description is presented for purposes of illustration and description of the various aspects of the invention. One of ordinary skill in the art will recognize that additional embodiments of the invention are possible without departing from the teachings herein. This detailed description, and particularly the specific details of the exemplary embodiments, is given primarily for clarity of understanding, and no unnecessary limitations are to be imported, for modifications will become obvious to those skilled in the art upon reading this disclosure and may be made without departing from the spirit or scope of the invention. Relatively apparent modifications, of course, include combining the various features of one or more figures with the features of one or more of other figures. All such modifications and variations are within the scope of the invention as determined by the appended claims when interpreted in accordance with the breadth to which they are fairly, legally and equitably entitled.

REFERENCES

Archer C and Francis-West P (2003) The chondrocyte. Int. J Biochem Cell Biol. 35, 401-404.

Brittberg, M, Lindahl, A, Nilsson, A, Ohlsson, C, Isakssin, O, Peterson, L. (1994) Treatment of deep cartilage defects in the knee with autologous chondrocyte transplantation. N Engl J Med. 331, 889-895.

Dowthwaite, G P, Flannery, C R, Lewthwaite, J, Flannelly, J, Archer, C W and Pitsillides A A. (2003) A mechanism underlying the movement requirement for synovial joint cavitation. Matrix Biol. 22, 311-322.

Dowthwaite, G P, Bishop J C, Redman S N, Khan I M, Rooney P, Evans D J, Haughton L, Bayram Z, Boyer S, Thomson B, Wolfe M S, Archer C W. (2004). The surface of articular cartilage contains a progenitor cell population. J Cell Sci. 117, 889-897

Hayes, A J, MacPherson, S, Morrison, H, Dowthwaite, G P and Archer, C W (2001). The development of articular cartilage: evidence for an appositional growth mechanism. Anat Embryol. 203, 469-79.

Knudson C B (2003). Hyaluronan and CD44: strategic players for cell-matrix interactions during chondrogenesis and matrix assembly. Birth Defects Res C Embryo Today. 69, 174-96.

Archer, C. W., McDowell, J., Bayliss, M. T., Stephens, M. D., Bentley, G., 1990. Phenotypic modulation in sub-populations of human articular chondrocytes in vitro. Journal of Cell Science 97, 361-371.

Barbero, A., Ploegert, S., Heberer, M. and Martin, I., 2003. Plasticity of clonal populations of dedifferentiated adult human articular chondrocytes. Arthritis and Rheumatism 48, 1315-1325.

Barnewitz. D., Endres, M., Kruger, I., Becker, A., Zimmermann, J., Wilke, I., Ringe, J., Sittinger, M., Kaps, C., 2006. Treatment of articular cartilage defects in horses with polymer-based cartilage tissue engineering grafts. Biomaterials 27, 2882-2889.

Craig, F. M., Bentley, G., Archer, C. W., (1987). The Spatial and Temporal Pattern of Collagen-I and Collagen-II and Keratan Sulfate in the Developing Chick Metatarsophalangeal Joint. Development 99, 383-391.

Frisbie, D. D., Trotter, G. W., Powers, B. E., Rodkey. W. G., Steadman, J. R., Howard. R. D., Park, R. D., McIlwraith, C. W., 1999. Arthroscopic subchondral bone plate microfracture technique augments healing of large chondral defects in the radial carpal bone and medial femoral condyle of horses. Veterinary Surgery 28, 242-255.

Frisbie, D. D., Oxford, J. T., Southwood, L., Trotter, G. W., Rodkey. W. G., Steadman, J. R., Goodnight, J. L., McIlwraith, C. W., 2003. Early events in cartilage repair after subchondral bone microfracture. Clinical Orthopaedics and Related Research 407, 215-227.

Frisbie, D. D., Bowman, S. M., Colhoun, H. A., DiCarol, E. F., Kawcak, C. E., McIlwraith, C. W., 2007. Evaluation of autologous chondrocyte transplantation via a collagen membrane in equine articular defects—results at 12 and 18 months. Osteoarthritis and Cartilage 16, 667-679.

Hoynowski, S. M., Fry, M. M., Gardner, B. M., Leming, M. T., Tucker, J. R., Black, L., Sand, T., Mitchell, K. E., 2007. Characterisation and differentiation of equine umbilical cord-derived matrix cells. Biochemical and Biophysical Research Communications 362, 347-353.

Janderova, L., McNeil, M., Murrell, A. N., Mynatt, R. L., and Smith, S. R., 2003. Human mesenchymal stem cells as an in vitro model for human adipogenesis. Obesity Research 11, 65-74.

Jones, P. H. and Watt, F. M., 1993. Separation of human epidermal stem cells from transit amplifying cells on the basis of differences in integrin function and expression. Cell 73, 713-724.

Koch, T. G., Heerkens, T., Thomsen, P. D., Betts, D. H., 2007. Isolation of mesenchymal stem cells from equine umbilical cord blood. BMC Biotechnology 7, 1-9.

Koerner, J., Nesic, D., Romero, J. D., Brehm, W., Mainil-Varlet, P., Grogan, S P., 2006. Equine peripheral blood-derived progenitors in comparison to bone marrow-derived mesenchymal stem cells. Stem Cells 24, 1613-1619.

Lefebvre, V. and Smits, P., 2005. Transcriptional control of chondrocyte fate and differentiation. Birth Defects Research 75, 200-212.

Marcacci, M., Kon, E., Moukhachev, V., Lavroukov, A., Kutepov, S., Quarto, R., Mastrogiacomo, M., Cancedda, R., 2007. Stem cells associated with macroporous bioceramics for long bone repair: 6- to 7-year outcome of a pilot clinical study. Tissue Engineering 13, 947-955.

Morishita, T., Honoki, K., Ohgushi, H., Kotobuki, N., Matsushima, A., Takakura, Y., 2006. Tissue engineering approach to the treatment of bone tumors: three cases of cultured bone grafts derived from patients' mesenchymal stem cells. Artificial Organs 30, 115-118.

Nixon A. J., Lust, G., Verniersinger. M., 1992. Isolation, Propagation, and Cryopreservation of Equine Articular Chondrocytes. American Journal of Veterinary Research 53, 2364-2370.

Oldershaw, R. A., Tew, S. R., Russell, A. M., Meade, K., Hawkins, R., McKay, T. R., Brennan, K. R., Hardingham, T. E., 2007. Notch signaling through Jagged-1 is necessary to initiate chondrogenesis in human bone marrow stromal cells, but must be switched off to complete chondrogenesis. Stem Cells 26, 1178-1188.

Pascucci, L., Marini, C., Mercati, F., Dal'aglio, C., Farneti, S., Ceccarelli, P., 2007. Adipose-derived mesenchymal stem cells in the horse: Isolation, in vitro expansion and preliminary identification in view of a possible use in the cellular therapy of tendon and ligament injuries. Ippologia 18, 13-18.

Quarto, R., Mastrogiacomo, M., Cancedda, R., Kutepov, S. M., Mukhachev, V., Lavroukov, A., Kon, E., Marcacci, M., 2001. Repair of large bone defects with the use of autologous bone marrow stromal cells. New England Journal of Medicine 344, 385-386.

Roberts, S., Hollander, A. P., Caterson, B., Menage, J., Richardson, J. B., 2001. Matrix turnover in human cartilage repair tissue in autologous chondrocyte implantation. Arthritis and rheumatism 44, 2586-98.

Roberts, S., McCall, I. W., Darby, A. J., Menage, J., Evans, H., Harrison, P. E., Richardson, J. B., 2003. Autologous chondrocyte implantation for cartilage repair: monitoring its success by magnetic resonance imaging and histology. Arthritis Research and Therapy 5, 60-73.

Singhrao, S. K., Müller, C. T., Gilbert, S. J., Duance, V. C., Archer, C. W., 2009. An immunofluorescence method for postembedded tissue in the acrylic resin Technovit 9100 New® using fluorescein isothiocyanate secondary detection.

Microscopy Research and Technique Published Online: Apr. 19 2009.

Stefan, A. J., Goletz, I., Klein, H., Stumpf, G., Beluche, L., Rohde, C., Addicks, K., Litzke, L. F., 2007. Isolation and characterisation of bone marrow-derived equine mesenchymal stem cells. American Journal of Veterinary Research. 68, 1095-1105. Vachon, A. M., McIlwraith, C. W., Powers, B. E., McFadden, P. R., Amiel, D., 1992. Morphologic and biochemical study of sternal cartilage autografts for resurfacing induced osteochondral defects in horses. American Journal of Veterinary Research. 53, 1038-1047

Williams, R., Nelson, L., Dowthwaite, G. P., Evans, D. J. R., Archer, C. W., 2009. Notch receptor and notch ligand expression in developing avain cartilage. Journal of Anatomy (in press).

Yang, R., Davies, C. M., Archer, C. W., Richards, R. G., 2003. Immunohistochemistry of matrix markers in Technovit 9100 New® embedded undecalcified bone sections. European Cells and Materials 6, 57-71.

What is claimed is:

1. A method of treating damaged cartilage in a horse, the method comprising:
   administering an isolated equine articular cartilage progenitor cell (ACPC) to damaged cartilage tissue in a horse such that cartilage is produced and the damaged cartilage tissue is functionally repaired, wherein said ACPC:
   a) is the equine progenitor cell population deposited under Accession No. 09101301 at the European Collection of Cell Cultures (ECACC);
   b) has a population doubling at a rate of approximately one population per day;
   c) has the ability to differentiate into chondrogenic, osteogenic, and adipogenic lineages; and
   d) expresses Type I and Type II collagen but not Type X collagen following chondrogenic differentiation.

2. The method of claim 1, wherein the damaged cartilage tissue is articular cartilage.

* * * * *